(12) United States Patent
Cho

(10) Patent No.: US 12,193,797 B2
(45) Date of Patent: Jan. 14, 2025

(54) ELECTRONIC DEVICE FOR MEASURING BLOOD PRESSURE AND METHOD FOR MEASURING BLOOD PRESSURE

(71) Applicant: Samsung Electronics Co., Ltd., Suwon-si (KR)

(72) Inventor: Sunghwan Cho, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 1224 days.

(21) Appl. No.: 16/824,174

(22) Filed: Mar. 19, 2020

(65) Prior Publication Data

US 2020/0297223 A1 Sep. 24, 2020

(30) Foreign Application Priority Data

Mar. 20, 2019 (KR) ........................ 10-2019-0032039

(51) Int. Cl.
*A61B 5/021* (2006.01)
*A61B 5/00* (2006.01)
*A61B 5/024* (2006.01)
*A61B 5/0295* (2006.01)
*A61B 5/25* (2021.01)

(52) U.S. Cl.
CPC ........ *A61B 5/02108* (2013.01); *A61B 5/0024* (2013.01); *A61B 5/02116* (2013.01); *A61B 5/02416* (2013.01); *A61B 5/0295* (2013.01); *A61B 5/25* (2021.01); *A61B 5/6802* (2013.01);
(Continued)

(58) Field of Classification Search
None
See application file for complete search history.

(56) References Cited

U.S. PATENT DOCUMENTS 6,868,419 B1    3/2005  Melick et al.
8,602,997 B2   12/2013  Banet et al.
(Continued)

FOREIGN PATENT DOCUMENTS

CN    101703396 A    5/2010
CN    102811659 A   12/2012
(Continued)

OTHER PUBLICATIONS

Zhang et al—Highly wearable cuff-less blood pressure and heart rate monitoring with single-arm electrocardiogram and photoplethysmogram signals; BioMed Eng OnLine (2017) 16:23 (Year: 2017).*
(Continued)

*Primary Examiner* — Jay B Shah
(74) *Attorney, Agent, or Firm* — Jefferson IP Law, LLP

(57) ABSTRACT

An electronic device is provided. The electronic device includes a display, a first sensor using a light source, a conductive, at least one processor, and a memory. The memory stores instructions that, when executed, cause the at least one processor to receive a first data from the first sensor, to receive a second data from at least one conductive electrode, to process the first data using a first pulse wave velocity (PWV) manner, based at least in part on a correlation of waveforms included in the first data, and to process the first data and the second data using a second PWV manner different from the first PWV manner, based at least in part on frequencies associated with the first data and the second data.

15 Claims, 11 Drawing Sheets

(52) U.S. Cl.
CPC ............ *A61B 5/7246* (2013.01); *A61B 5/742* (2013.01); *A61B 2562/0219* (2013.01)

(56) References Cited

U.S. PATENT DOCUMENTS

| | | |
|---|---|---|
| 8,672,855 B2 | 3/2014 | Fayram et al. |
| 9,022,945 B2 | 5/2015 | Fayram et al. |
| 10,045,700 B2 | 8/2018 | Noh et al. |
| 10,448,830 B2 | 10/2019 | Knickerbocker et al. |
| 10,531,797 B2 | 1/2020 | Knickerbocker et al. |
| 10,820,811 B2 | 11/2020 | Hubner |
| 2010/0160798 A1 | 6/2010 | Banet et al. |
| 2011/0009712 A1 | 1/2011 | Fayram et al. |
| 2013/0296723 A1 | 11/2013 | Cho et al. |
| 2014/0155707 A1 | 6/2014 | Fayram et al. |
| 2017/0042433 A1 | 2/2017 | Noh et al. |
| 2017/0112395 A1 | 4/2017 | Kim et al. |
| 2017/0202459 A1 | 7/2017 | Cao |
| 2017/0340219 A1 | 11/2017 | Sullivan et al. |
| 2018/0078153 A1 | 3/2018 | Knickerbocker et al. |
| 2018/0078154 A1 | 3/2018 | Knickerbocker et al. |
| 2018/0199893 A1 | 7/2018 | Hubner |
| 2018/0214037 A1 | 8/2018 | Hubner |
| 2018/0256044 A1 | 9/2018 | Goodman et al. |
| 2022/0296176 A1 | 9/2022 | Hubner |

FOREIGN PATENT DOCUMENTS

| | | |
|---|---|---|
| CN | 103690152 A | 4/2014 |
| CN | 107920763 A | 4/2018 |
| EP | 3061391 A1 | 8/2016 |
| JP | 2014-000105 A | 1/2014 |
| KR | 10-2013-0123597 A | 11/2013 |
| KR | 10-2017-0019189 A | 2/2017 |
| KR | 10-2017-0048970 A | 5/2017 |
| WO | 2015-171667 A1 | 11/2015 |
| WO | 2016/065469 A1 | 5/2016 |

OTHER PUBLICATIONS

Chinese Office Action dated Jul. 6, 2023, issued in Chinese Patent Application No. 202080022904.8.

International Search Report dated Jul. 8, 2020, issued in International Application No. PCT/KR2020/003795.

* cited by examiner

ELECTRONIC DEVICE FOR MEASURING BLOOD PRESSURE AND METHOD FOR MEASURING BLOOD PRESSURE

CROSS-REFERENCE TO RELATED APPLICATION(S)

This application is based on and claims priority under 35 U.S.C. § 119(a) of a Korean patent application number 10-2019-0032039, filed on Mar. 20, 2019, in the Korean Intellectual Property Office, the disclosure of which is incorporated by reference herein in its entirety.

BACKGROUND

1. Field

The disclosure relates to an electronic device for measuring blood pressure of a user and a method for measuring the blood pressure.

2. Description of Related Art

Various mobile electronic devices, such as smart phones, tablet personal computers (PCs), smart watches, or smart bands have been released. The electronic device may perform various functions, such as a call, internet search, video playback, and music playback. Recently, the electronic device may obtain biometric information of a user by using various sensors and may provide various health-related information, based on the obtained biometric information.

For example, the electronic device may calculate a blood flow rate of the user through a sensor and may calculate and display the blood pressure of the user, based on the blood flow rate. The user may check his/her health state through the displayed blood pressure.

The above information is presented as background information only to assist with an understanding of the disclosure. No determination has been made, and no assertion is made, as to whether any of the above might be applicable as prior art with regard to the disclosure.

SUMMARY

When measuring blood pressure in a non-pressure manner (cuffless), an electronic device uses one of a method using a single photoplethysmography (PPG) sensor and a method using both the PPG sensor and an electrocardiography (ECG) sensor according to the related art.

A measurement method using the single photoplethysmography (PPG) sensor uses a PPG single signal. Therefore, the measurement is relatively convenient, and the measurement may be performed even in a user's unconscious state. Among the measurement methods using only the PPG sensor, an Aortic Pulse Wave Velocity (AoPWV) is not uniform in a measurement accuracy depending on a signal quality and is greatly influenced by external environmental factors (e.g., a measurement posture and a temperature).

On the other hand, in the measurement method using both the PPG sensor and the ECG sensor, a blood flow rate is estimated by calculating the distance between a systolic point (R-peak) of the heart and a peak of the PPG signal. A pulse arrival time (PAT) method, which uses both the PPG sensor and the ECG sensor, is relatively easy to calculate the blood flow rate, the PAT method is less affected by external noises and obtains uniform measurement values. However, because the PAT method estimates blood pressure by using different mechanisms for various cases of increase in blood pressure, calculation accuracy is lowered.

Aspects of the disclosure are to address at least the above-mentioned problems and/or disadvantages and to provide at least the advantages described below. Accordingly, an aspect of the disclosure is to provide an electronic device for measuring blood pressure of a user and a method for measuring the blood pressure.

Additional aspects will be set forth in part in the description which follows and, in part, will be apparent from the description, or may be learned by practice of the presented embodiments.

In accordance with an aspect of the disclosure, an electronic device is provided. The electronic device includes a housing, a display that is visible through a first portion of the housing, a first sensor that uses a light source that is exposed through a second portion of the housing, at least one conductive electrode that is disposed outside the housing or on the display, a processor that is disposed inside the housing and operatively connected to the first sensor, the at least one conductive electrode, and the display, and a memory that is disposed inside the housing and operatively connected to the processor, and wherein the memory stores instructions that, when executed, cause the processor to receive first data from the first sensor, to receive second data from the at least one conductive electrode, to process the first data by using a first pulse wave velocity (PWV) manner, based at least in part on a correlation of waveforms included in the first data, to process the first data and the second data by using a second PWV manner different from the first PWV manner, based at least in part on frequencies associated with the first data and the second data, to calculate a first weight associated with the first PWV manner and a second weight associated with the second PWV manner, based at least in part on a ratio of the waveforms included in the first data, to calculate a blood pressure value, based at least in part on the first weight and the second weight, and to display the calculated blood pressure on the display.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

Figure 1:
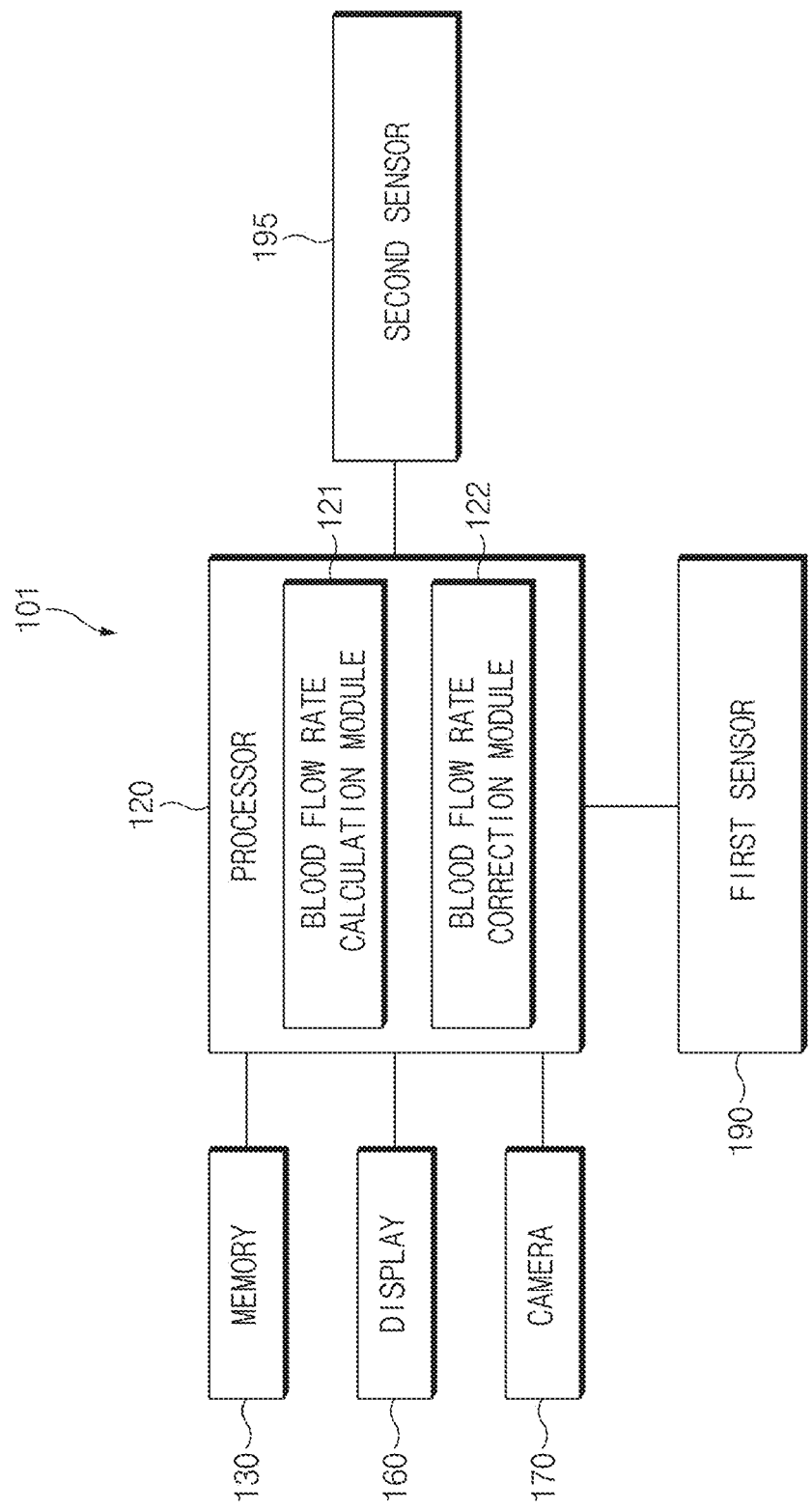
FIG. 1 is a block diagram illustrating an electronic device according to an embodiment of the disclosure.

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

In the disclosure, the expressions "have", "may have", "include" and "comprise", or "may include" and "may comprise" used herein indicate existence of corresponding features (e.g., components, such as numeric values, functions, operations, or parts) but do not exclude presence of additional features.

In the disclosure, the expressions "A or B", "at least one of A or/and B", or "one or more of A or/and B", and the like may include any and all combinations of one or more of the associated listed items. For example, the term "A or B", "at least one of A and B", or "at least one of A or B" may refer to all of the case (1) where at least one A is included, the case (2) where at least one B is included, or the case (3) where both of at least one A and at least one B are included.

The terms, such as "first", "second", and the like used in the disclosure may be used to refer to various components regardless of the order and/or the priority and to distinguish the relevant components from other components, but do not limit the components. For example, "a first user device" and "a second user device" indicate different user devices regardless of the order or priority. For example, without departing the scope of the disclosure, a first component may be referred to as a second component, and similarly, a second component may be referred to as a first component.

It will be understood that when a component (e.g., a first component) is referred to as being "(operatively or communicatively) coupled with/to" or "connected to" another component (e.g., a second component), it may be directly coupled with/to or connected to the other component or an intervening component (e.g., a third component) may be present. In contrast, when a component (e.g., a first component) is referred to as being "directly coupled with/to" or "directly connected to" another component (e.g., a second component), it should be understood that there are no intervening component (e.g., a third component).

According to the situation, the expression "configured to" used in the disclosure may be used as, for example, the expression "suitable for", "having the capacity to", "designed to", "adapted to", "made to", or "capable of". The term "configured to" must not mean only "specifically designed to" in hardware. Instead, the expression "a device configured to" may mean that the device is "capable of" operating together with another device or other parts. For example, a "processor configured to (or set to) perform A, B, and C" may mean a dedicated processor (e.g., an embedded processor) for performing a corresponding operation or a generic-purpose processor (e.g., a central processing unit (CPU) or an application processor) which performs corresponding operations by executing one or more software programs which are stored in a memory device.

Terms used in the disclosure are used to describe specified embodiments and are not intended to limit the scope of the disclosure. The terms of a singular form may include plural forms unless otherwise specified. All the terms used herein, which include technical or scientific terms, may have the same meaning that is generally understood by a person skilled in the art. It will be further understood that terms, which are defined in a dictionary and commonly used, should also be interpreted as is customary in the relevant related art and not in an idealized or overly formal unless expressly so defined in various embodiments of the disclosure. In some cases, even if terms are terms which are defined in the disclosure, they may not be interpreted to exclude embodiments of the disclosure.

According to various embodiments of the disclosure, the wearable device may include at least one of an accessory type (e.g., watches, rings, bracelets, anklets, necklaces, glasses, contact lens, or head-mounted-devices (HMDs)), a fabric or garment-integrated type (e.g., an electronic apparel), a body-attached type (e.g., a skin pad or tattoos), or a bio-implantable type (e.g., an implantable circuit).

Hereinafter, electronic devices according to various embodiments will be described with reference to the accompanying drawings. In the disclosure, the term "user" may refer to a person who uses an electronic device or may refer to a device (e.g., an artificial intelligence electronic device) that uses the electronic device.

FIG. 1 is a block diagram illustrating an electronic device according to an embodiment of the disclosure. FIG. 1 illustrates a configuration, and the disclosure is not limited thereto. For example, some components may be added in FIG. 1 or may be excluded from FIG. 1. A first sensor and a second sensor may be implemented as one device.

Referring to FIG. 1, a configuration of an electronic device according to various embodiments is illustrated. Components associated with calculating a blood flow rate are illustrated in FIG. 1, but the disclosure is not limited thereto. Some components included in FIG. 1 may be omitted, or other components may be added in FIG. 1.

Referring to FIG. 1, an electronic device 101 may include a processor 120, a memory 130, a display 160, a camera 170, a first sensor 190, and a second sensor 195.

The processor 120 may be operationally connected with the memory 130, the display 160, the camera 170, the first sensor 190, and the second sensor 195. The processor 120 may perform an operation required for an operation of the electronic device 101.

According to various embodiments of the disclosure, the processor 120 may include a blood flow rate calculation module 121 and a blood flow rate correction module 122.

According to various embodiments of the disclosure, the blood flow rate calculation module 121 may measure a blood flow rate by using at least one of a first manner (e.g., AoPWV) and a second manner (e.g., PAT).

The first manner may be a manner of calculating a first blood flow rate, based on first sensing information obtained by using a first sensor (e.g., a photoplethysmography (PPG) sensor) 181. According to the first manner, when light (e.g., infrared radiation (IR) Red/Blue/Green) emitted from a light source is partially absorbed and partially reflected at blood vessels in a skin, the amount of the reflected light may be detected through a light receiver, and a waveform in which a change in amplitude is repeated depending on a movement of a heart may be obtained.

The first manner may calculate the blood flow rate that is highly correlated with the blood pressure by calculating a time difference between the first inflection point and the second inflection point in a pulse waveform. For example, the first manner that is a manner of calculating a pulse speed by analyzing the waveform of the PPG signal may calculate the pulse speed, based on a distance between peaks in a single waveform.

Because the first manner uses a single PPG signal, the measurement is convenient and may be performed even in the unconscious state of the user. In the first manner, a measurement accuracy may not be uniform depending on a signal quality and may be greatly influenced by external environmental factors (measurement posture and temperature).

The second manner may be a manner of calculating a second blood flow rate, based on first sensing information obtained by using the first sensor (e.g., the PPG sensor) 190 and second sensing information obtained by using the second sensor (e.g., the ECG sensor) 195.

The second manner (e.g., the PAT manner) may estimate the blood flow rate by calculating a distance between a systolic point (R-peak) of the heart and a peak of the PPG signal, based on signals obtained from the PPG and ECG sensors. For example, in the second manner (e.g., the PAT manner), the pulse wave moving time may be measured by using a difference between a departure time and an arrival time of the pulse wave. More particularly, the blood flow rate may be calculated by defining the R-peak of the ECG as a starting point of the pulse wave, and by defining a first peak of the PPG as an arrival point of the pulse wave.

The second manner (e.g., the PAT manner) that is a manner of calculating the blood pressure by finding the highest point of the ECG and PPG signal may make it easy to calculate the blood pressure. In addition, because the second manner has a small influence of external noise, the second manner may make it possible to obtain a uniform measurement value. In the second manner (e.g., the PAT manner), a calculation accuracy may be lowered because the blood pressure is estimated by different mechanisms for respective cases in which the blood pressure increases.

Figure 5:
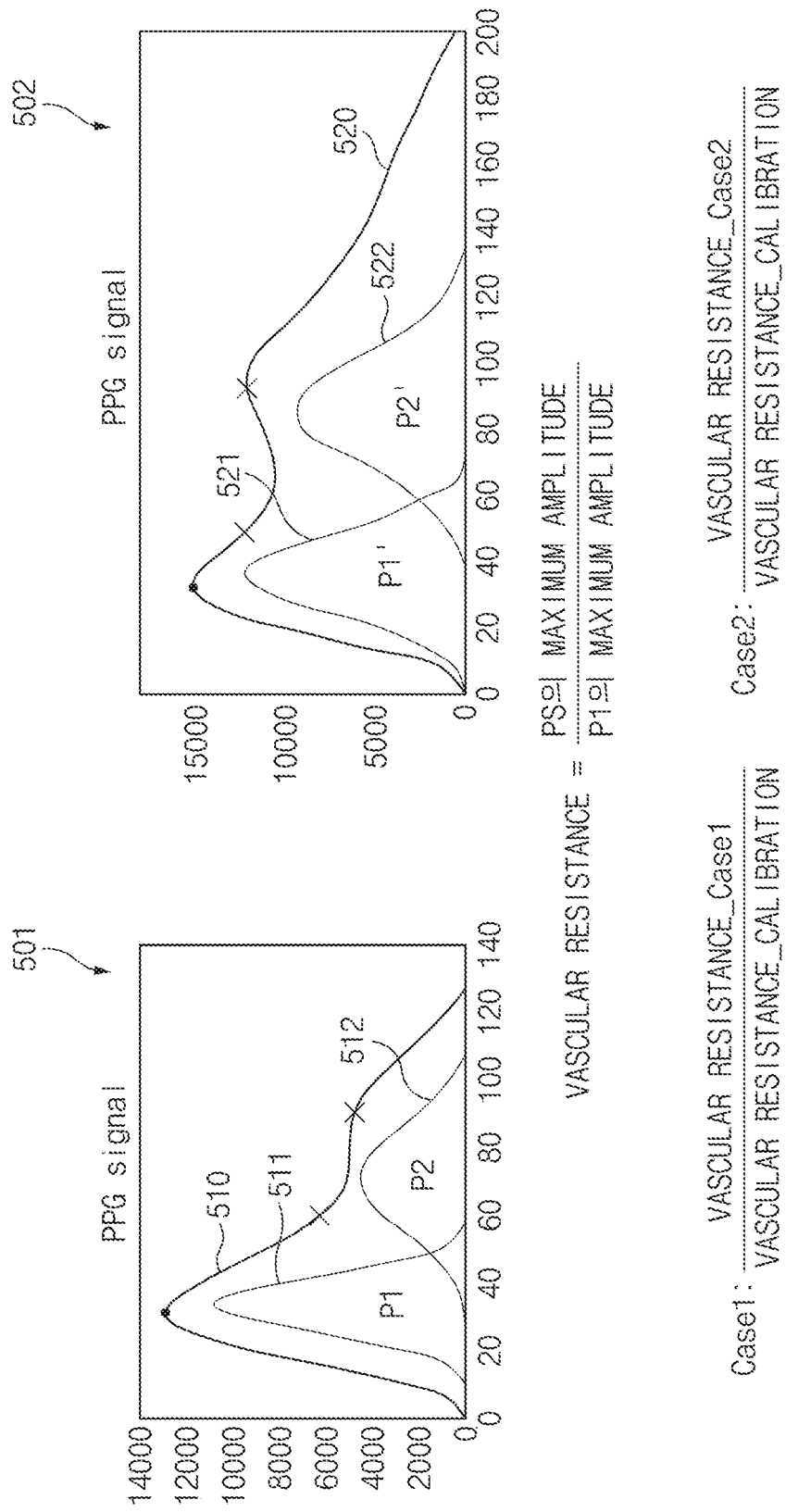
FIG. 5 is a diagram illustrating how to calculate a weight by using vascular resistance parameters, according to an embodiment of the disclosure.
Figure 6:
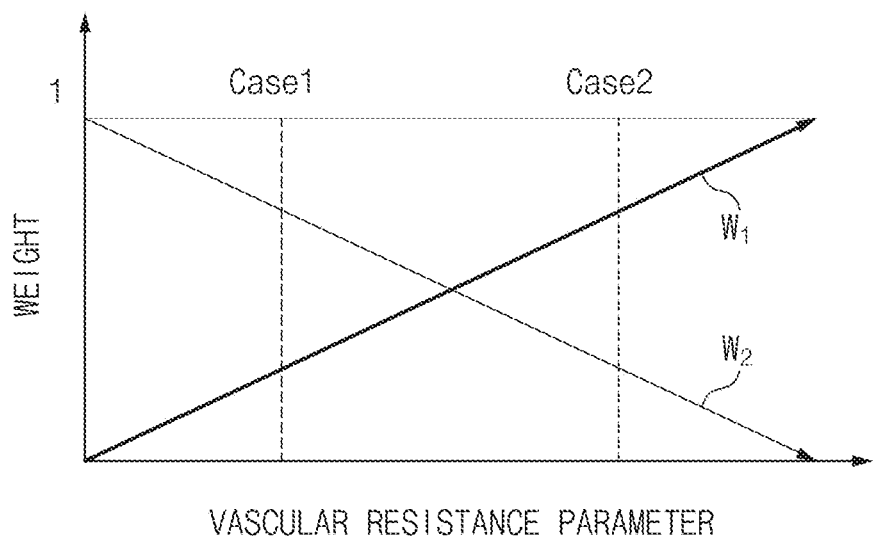
FIG. 6 is a diagram illustrating how to calculate a weight based on vascular resistance parameters, according to an embodiment of the disclosure.

According to various embodiments of the disclosure, based on a parameter related to a blood vessel resistance, the blood flow rate correction module 122 may determine a weight of the first blood flow rate by the first manner and a weight of the second blood flow rate by the second manner and may determine corrected blood flow rate (refer to FIGS. 5 and 6).

The memory 130 may store various information required for an operation of the electronic device 101. According to an embodiment of the disclosure, the memory 130 may store information about a user's health. For example, the memory 130 may store information about a height, weight, blood pressure, and body temperature.

According to various embodiments of the disclosure, the memory 130 may store a blood pressure value or a posture information value when calibration is made by the user.

According to various embodiments of the disclosure, the memory 130 may store the blood pressure value of the user, which is measured in a pressurized manner (e.g., Cuff), or may store or update an absolute blood pressure value of the user, which is received from an external device (e.g., a server of an external medical institution or a server of an insurance company).

The display 160 may provide various information to the user through text, an image, or a user interface. For example, the display 160 may provide the user with a guide on the posture of blood pressure measurement.

According to various embodiments of the disclosure, the display 160 may display health information of the user. For example, the display 160 may display the user's blood pressure value in a numerical value, level, or graph.

The camera 170 may obtain image data by using an image sensor. For example, the camera 170 may be used when a user's posture is to be checked.

According to various embodiments of the disclosure, the electronic device 101 may further include an audio module (e.g., a microphone). The audio module (e.g., a microphone) may be used to measure a distance between the user and the electronic device 101.

The first sensor 190 may include a sensor that obtains biometric information by using the light source. The first sensor 190 may include a light source unit, a light receiver, and a control circuit (refer to FIG. 2). The first sensor 190 may obtain first sensing information (e.g., PPG sensing information). The first sensing information (e.g., PPG sensing information) may be used in both the first manner and the second manner of calculating the blood flow rate.

The second sensor 195 may be an electrocardiogram (ECG) sensor including a plurality of electrodes. When a part of the user's body contacts the plurality of electrodes, the second sensor module may measure the second sensing information (e.g., ECG), based on an electrical signal flowing through the electrodes.

The case where the electronic device 101 includes the first sensor 190 and the second sensor 195 is illustrated in FIG. 1, but the disclosure is not limited thereto. For example, the electronic device 101 may include electrodes for measuring various biometric information (e.g., galvanic skin response (GSR), electroencephalography (EEG), and bioelectrical impedance analysis (BIA)). For another example, the electronic device 101 may include an acceleration sensor, a proximity sensor, a gyro sensor, a temperature (body temperature) sensor, an iris sensor, and the like, to obtain information about a surrounding situation of the user. For another example, the electronic device 101 may include a temperature/humidity sensor, an illuminance sensor, a time of flight (TOF) sensor, an ultra-wideband (UWB), a gas sensor, a fine dust sensor, and the like, to determine an external environment.

According to various embodiments of the disclosure, the electronic device 101 may include a communication module (e.g., cellular communication, global positioning system (GPS), or wireless-fidelity (Wi-Fi)) to obtain information of a situation related to the user or the electronic device.

According to various embodiments of the disclosure, the electronic device 101 may further include a housing (not illustrated) for mounting the components of FIG. 1. The processor 120 and the memory 130 may be mounted on a printed circuit board (PCB) inside the housing. At least a portion of the display 160 may be viewable through a first portion (e.g., a front surface) of the housing. The first sensor (e.g., the PPG sensor) 190 may be exposed through a second portion (e.g., a rear surface) of the housing.

According to various embodiments of the disclosure, the electronic device 101 may further include at least one conductive electrode that is disposed outside the housing or on the display 160. The at least one conductive electrode may be electrically connected to the second sensor (e.g., the ECG sensor) 195.

According to various embodiments of the disclosure, the electronic device 101 may further include an acceleration sensor and a gyro sensor, which are located inside the housing. The processor 120 may estimate the blood pressure value, based on at least one of an acceleration sensor value or a gyro sensor value. The processor 120 may determine the posture of the user by using the acceleration sensor and the gyro sensor.

Figure 2:
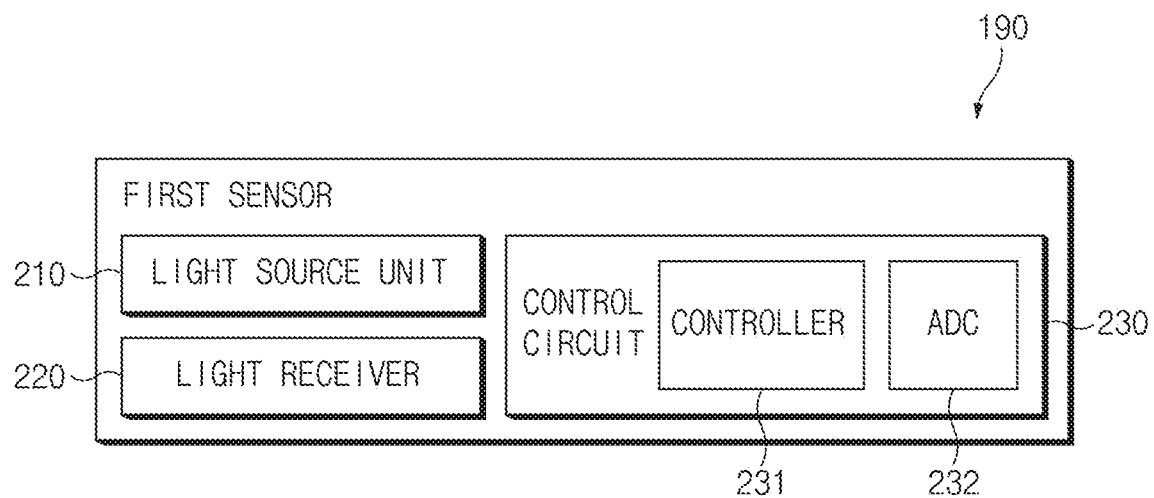
FIG. 2 is a diagram illustrating a first sensor according to an embodiment of the disclosure.

FIG. 2 is a diagram illustrating a first sensor according to an embodiment of the disclosure.

Referring to FIG. 2, the first sensor 190 may be a sensor that outputs light by using a light source and obtains biometric information of the user by obtaining the reflected light.

According to various embodiments of the disclosure, the first sensor 190 may include a light source unit 210, a light receiver 220, and a control circuit 230.

The light source unit 210 may include a light source (e.g., a light emitting diode (LED)) having a plurality of different wavelengths. The light that is output from the light source unit 210 may be reflected by an external object (e.g., a skin of the user).

For example, light of a green wavelength that is output from the light source unit 210 may be used to measure a heart rate. The light of the green wavelength may penetrate shallowly into the user's skin and may be robust against noise. Light of a red wavelength that is output from the light source unit 210 may penetrate relatively deep into the skin and may be used to more accurately measure the heart rate. In addition to the light of the red wavelength, light of an IR wavelength output from the light source unit 210 may be used to obtain more biometric information, such as a heart rate and a SPO2. According to an embodiment of the disclosure, the processor 120 may measure a skin tone of the user by using light sources that output light of red, green, and IR wavelengths.

For another example, light of a blue wavelength that is output from the light source unit 210 may be used to measure blood glucose.

According to various embodiments of the disclosure, the light source unit 210 may include LED light sources of various wavelength bands. As a wavelength band capable of being output from the light source unit 210 is added, more biometric information about the user may be obtained. The light source unit 210 may include at least one or more emitters for each wavelength.

The light receiver 220 may include at least one or more photodiodes. The light receiver 220 may include one or more light receivers that are disposed to have the same specified separation distance from the light sources of the light source unit 210 or to have different separation distances therefrom.

According to various embodiments of the disclosure, the light source unit 210 may be implemented with a laser diode (LD). The light receiver 220 may be an image sensor that receives light that is output from the laser diode (LD) and is reflected from a part of a living body (e.g., a blood vessel).

The control circuit 230 may control operations of the light source unit 210 and the light receiver 220. According to an embodiment of the disclosure, the control circuit 230 may include a sensor driver controller 231 to directly control a sensor and an analog-to-digital (ADC) 232 to convert an analog signal into a digital signal.

The sensor driver controller 231 may include a light source controller to control a light source (emitter) and a light receiving controller to control a detector.

According to an embodiment of the disclosure, the sensor driver controller 231 may perform a function of an AFE. The AFE may include an amplifier to amplify values of LED drivers and the detector, an ADC to convert an analog value output from the detector into a digital value, and a controller to control the LED drivers and the ADC.

According to various embodiments of the disclosure, the control circuit 230 may process light received through the light receiver 220, by using various filters and an analog digital converter (ADC) and may transmit the processed result to the processor 120. The processor 120 may receive the first sensing information provided from the first sensor 190 and may extract the biometric value, which is a target value to be measured through a specified algorithm. The extracted biometric information may be provided to the user or may be stored for an application related to a health care. Alternatively, the extracted biometric information may be transmitted to an external server.

Figure 3A:
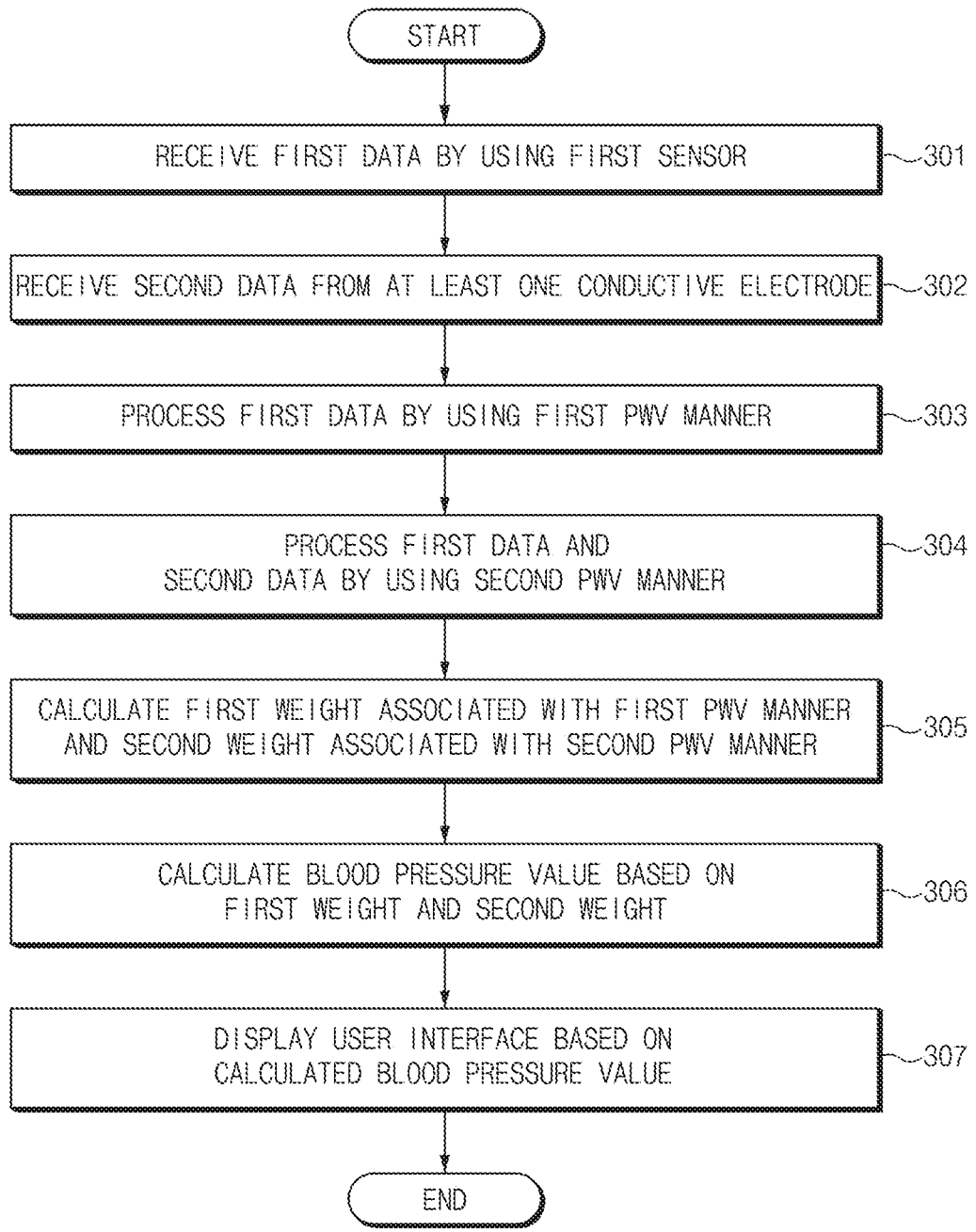
FIG. 3A is a flowchart illustrating a blood pressure measuring method according to an embodiment of the disclosure.

FIG. 3A is a flowchart illustrating a blood pressure measuring method according to an embodiment of the disclosure.

Referring to FIG. 3A, in operation 301, the processor 120 may receive first data (e.g., a PPG value) by using the first sensor 190 (e.g., a PPG sensor). When light (e.g., IR/red/blue/green) emitted from a light source is partially absorbed and partially reflected by blood vessels in the skin, the first sensor 190 (e.g., a PPG sensor) may receive the first data by sensing the amount of reflected light through the light receiver.

In operation 302, the processor 120 may receive second data (e.g., ECG) from at least one conductive electrode that is disposed outside the housing or on a display. The at least one conductive electrode may be exposed to the outside of the electronic device 101 and may be in contact with the user's body. When a part of the user's body is in contact with the at least one conductive electrode, the processor 120 may measure the electrocardiogram (e.g., ECG), based on an electrical signal transmitted through the electrodes.

In operation 303, the processor 120 may process the first data by using a first pulse wave velocity (PWV) manner, based at least in part on a correlation of waveforms included in the first data. The first PWV manner may be an Ao (Aortic) PWV manner. The AoPWV manner may obtain a blood flow rate highly correlated with blood pressure by calculating a time difference between a first inflection point and a second inflection point in the pulse waveform.

In operation 304, the processor 120 may process the first data and the second data by using a second PWV manner different from the first PWV manner, based at least in part on frequencies associated with the first data and the second data. The second PWV manner may be a pulse arrival time (PAT) PWV manner. The PAT PWV manner may estimate the blood flow rate by calculating a distance between the systolic point (R-peak) of the heart and the peak of the PPG signal, based at least in part on the first data (e.g., the PPG) and the second data (e.g., ECG).

According to various embodiments of the disclosure, the processor 120 may compare the correlation of the waveforms included in the first data with a first threshold. When the correlation is greater than the first threshold as similarity between the waveforms is high, the processor 120 may determine the first data as a valid value and may use the first data to calculate the blood flow rate depending on the first PWV manner (e.g., AoPWV).

According to various embodiments of the disclosure, the processor 120 may compare magnitudes of the frequencies associated with the first data and the second data with a second threshold. When the magnitude of a frequency capable of measuring the blood flow rate is greater than the second threshold, the processor 120 may determine the first data as a valid value, and may use the first data to calculate the blood flow rate depending on the second PWV manner (e.g., the PAT).

According to various embodiments of the disclosure, the processor 120 may provide a notification through the user interface when the correlation of the waveforms is less than the first threshold value and the magnitudes of the frequencies are less than the second threshold value.

In operation 305, the processor 120 may calculate a first weight associated with the first PWV manner and a second weight associated with the second PWV manner, based at least in part on a ratio of the waveforms included in the first data. The processor 120 may determine the first weight and the second weight, based on a parameter related to a vascular resistance. The parameter related to the vascular resistance may be determined based on waveform characteristics of the first data (refer to FIGS. 5 and 6).

In operation 306, the processor 120 may calculate the blood pressure value, based at least in part on the first weight and the second weight. The first weight and the second weight may be inversely proportional to each other, a sum of the first weight and the second weight may be maintained at a uniform value.

In operation 307, the processor 120 may display a user interface on the display 160, based at least in part on the calculated blood pressure. For example, the processor 120 may display the user interface by using graphics or text and may allow the user to recognize the calculated blood pressure.

Figure 3B:
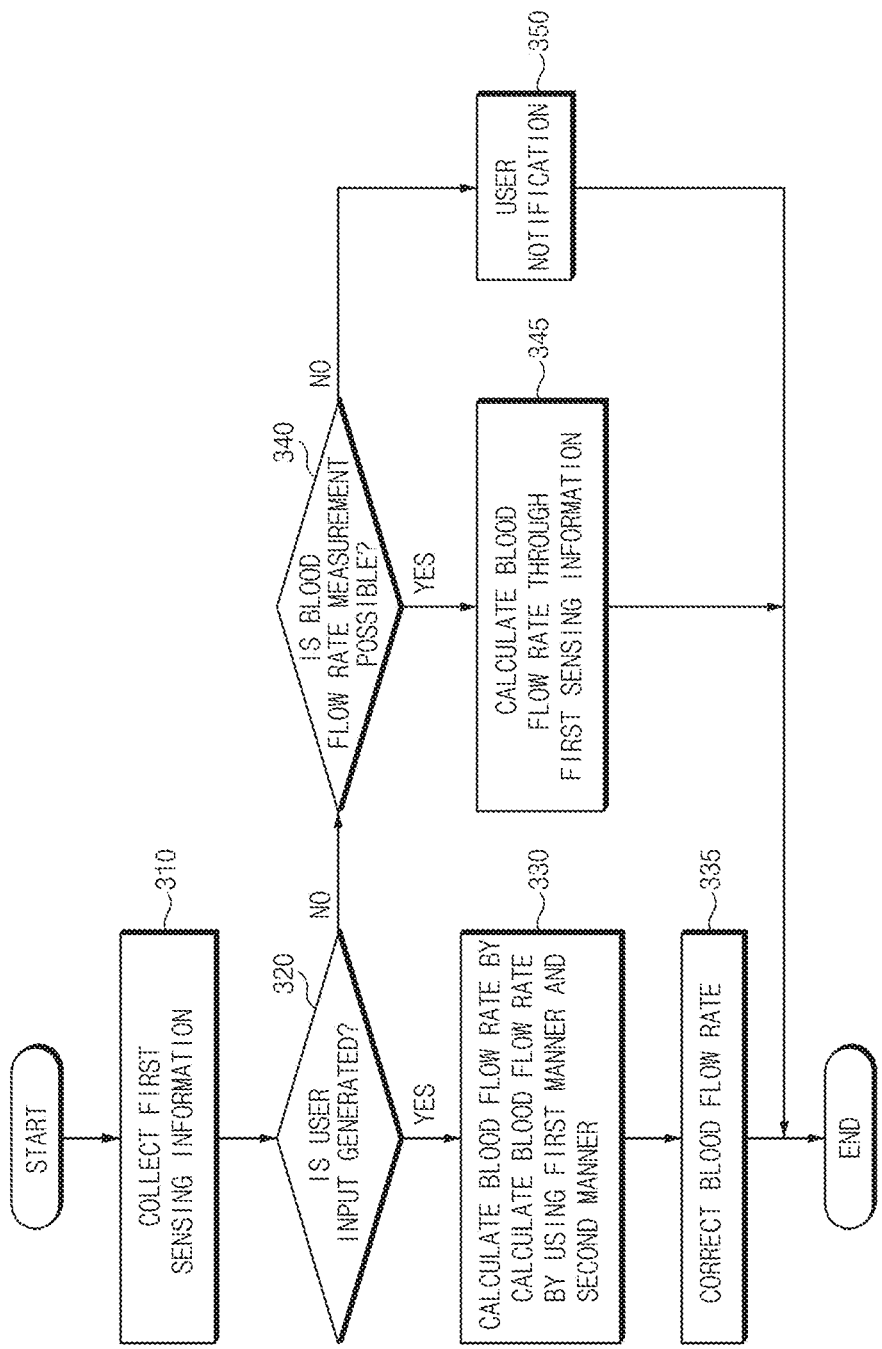
FIG. 3B is a flowchart illustrating how to start to measure blood pressure in response to a user input, according to an embodiment of the disclosure.

FIG. 3B is a flowchart illustrating how to start to measure blood pressure in response to a user input, according to an embodiment of the disclosure.

Referring to FIG. 3B, in operation 310, the processor 120 may obtain first sensing information (e.g., a PPG value) by using the first sensor 190. For example, in the case where the electronic device 101 is a smart watch, the processor 120 may output light at a specified cycle by using a light source of a PPG sensor that is disposed on an opposite surface to a display surface. When the user wears or uses the electronic device 101, the processor 120 may automatically obtain the first sensing information (e.g., a PPG value) without a separate user input.

In operation 320, the processor 120 may determine whether a separate user input for obtaining the second sensing information (e.g., an ECG value) by using the second sensor 195 is generated. For example, the user input may be generated when the user touches his/her body part on each of the plurality of electrodes for a specified time or more.

Figure 4:
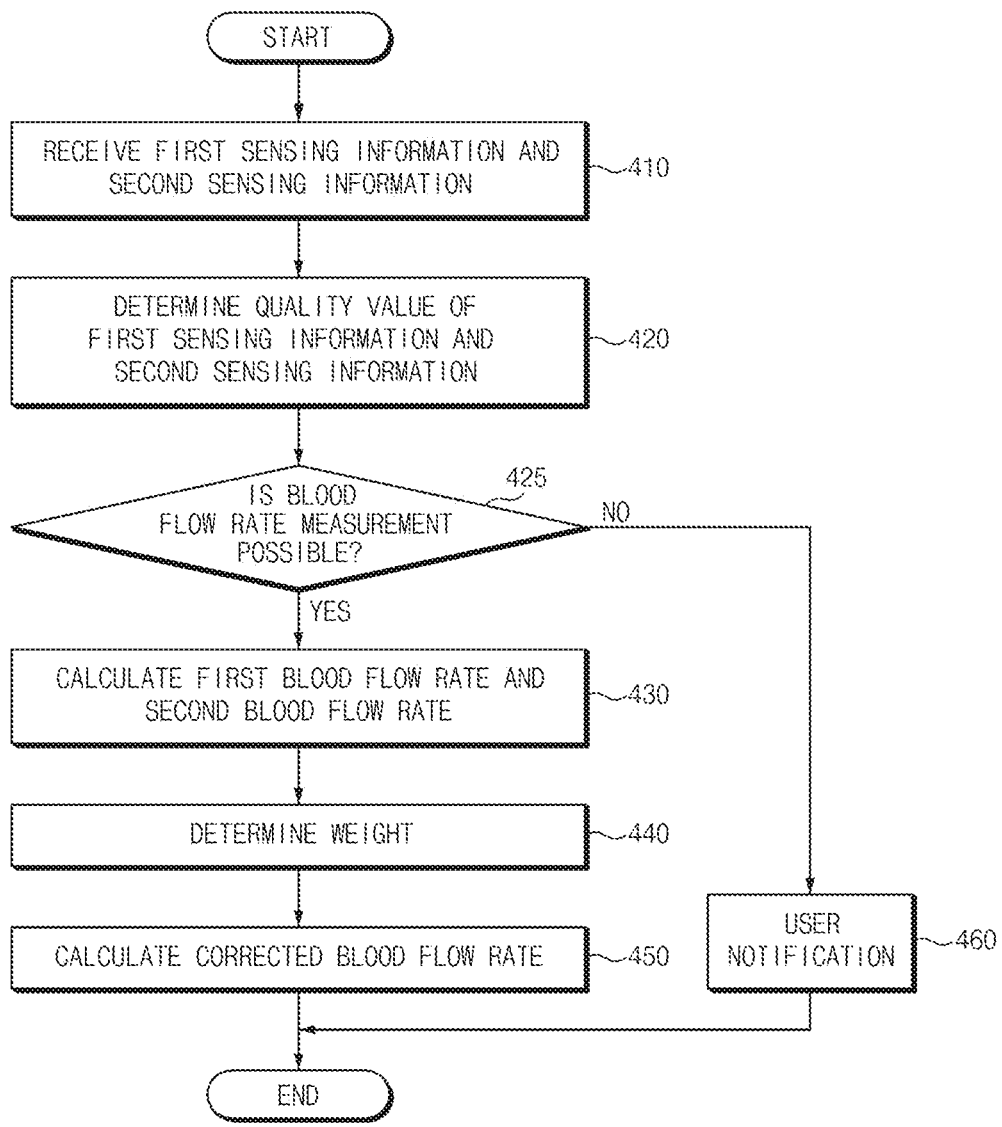
FIG. 4 is a flowchart illustrating a blood pressure measuring method according to an embodiment of the disclosure.

In operation 330, when the separate user input for obtaining second sensing information (e.g., an ECG value) by using the second sensor 195 is generated, the processor 120 may calculate the blood flow rate, based on the first manner and the second manner, respectively (refer to FIG. 4).

In operation 335, the processor 120 may correct the blood flow rate by using a parameter related to a vascular resistance. The parameter related to the vascular resistance may be calculated by analyzing a waveform of the first sensing information (refer to FIGS. 5 and 6).

In operation 340, when the separate user input is not generated, the processor 120 may determines whether the blood flow rate is measurable through the first sensing information (e.g., a PPG value).

When the blood flow rate is measurable through the first sensing information (e.g., a PPG value), in operation 345, the processor 120 may calculate the blood flow rate by using the first manner and may measure the blood pressure of the user, based on the calculated blood flow rate. In this case, the processor 120 may periodically measure the blood pressure of the user without generating a separate user notification.

In operation 350, when it is impossible to measure the blood flow rate through the first sensing information (e.g., a PPG value), the processor 120 may notify the user that the blood pressure is not measured through the notification.

FIG. 4 is a flowchart illustrating a blood pressure measuring method according to an embodiment of the disclosure.

Referring to FIG. 4, in operation 410, the processor 120 may receive first sensing information and second sensing information from the first sensor 190 and the second sensor 195, respectively.

The first sensor 190 may obtain the first sensing information by outputting light through a light source and receiving light reflected from an external object (e.g., a user's body).

The second sensor 195 may be an electrocardiogram sensor including a plurality of electrodes. The second sensor 195 may measure the second sensing information (e.g., ECG information or ECG), based on an electrical signal transmitted through the electrodes, when the user touches his/her body part on each of the electrodes.

According to various embodiments of the disclosure, the first sensing information may be measured in a state where the user does not recognize the measurement. For example, when the user is wearing a wearable device, the wearable device may periodically output light of a specified wavelength through the light source unit. The biometric information of the user may be obtained based on a reflection light that is reflected by the external object after the light is output.

According to various embodiments of the disclosure, the second sensing information may be obtained when a separate application is executed or when a specified user input occurs (e.g., when a state in which a touch is made on the plurality of electrodes is maintained for a preset time or more)

In operation 420, the processor 120 may determine a quality value of the first sensing information (e.g., a PPG) and a quality value of the second sensing information (e.g., ECG). The quality value is a value for the calculation of the blood flow rate.

In operation 425, the processor 120 may determine whether each of the first sensing information (e.g., the PPG) and the second sensing information (e.g., ECG) has the quality value capable of calculating the blood flow rate.

According to one embodiment of the disclosure, when the first sensing information (e.g., a PPG) or the second sensing information (e.g., ECG) is not obtained or is different from a pattern stored in advance, the processor 120 may determine that the determined quality value is a value incapable of calculating the blood flow rate. When the first sensing information (e.g., a PPG) or the second sensing information (e.g., ECG) is obtained and has high similarity to the pattern stored in advance, the processor 120 may determine that the determined quality value is a value capable of calculating the blood flow rate.

In operation 430, when each of the first sensing information (e.g., a PPG) and the second sensing information (e.g., ECG) received within a specified time interval has a quality value capable of calculating the blood flow rate, the processor 120 may calculate the first blood flow rate and the second blood flow rate by using the first manner and the second manner, respectively.

The processor 120 may calculate the first blood flow rate in the first manner by using the first sensing information (e.g., a PPG). The processor 120 may calculate the second blood flow rate in the second manner by using the first sensing information (e.g., a PPG) and the second sensing information (e.g., ECG).

In operation 440, the processor 120 may determine a weight of each of the first blood flow rate and the second blood flow rate, based on a parameter related to a vascular resistance. The parameter related to the vascular resistance may be determined based on waveform characteristics of the first sensing information (refer to FIGS. 5 and 6).

In operation 450, the processor 120 may calculate a corrected blood flow rate, based on the weight of each of the first blood flow rate and the second blood flow rate. The processor 120 may calculate the blood pressure value of the user, based on the corrected blood flow rate.

In operation 460, when at least one of the first sensing information (e.g., a PPG) or the second sensing information (e.g., ECG) does not have a quality value capable of calculating the blood flow rate, the processor 120 may provide a notification that the blood pressure measurement is impossible through a user notification. Alternatively, when the first sensing information (e.g., a PPG) is valid, the processor 120 may calculate the blood flow rate in the first manner by using the first sensing information (e.g., a PPG).

FIG. 5 is a diagram illustrating how to calculate a weight by using vascular resistance parameters, according to an embodiment of the disclosure.

Referring to FIG. 5, the processor 120 may determine a parameter (hereinafter referred to as a "vascular resistance parameter") that indicates a vascular resistance by analyzing a waveform of a pulse that is received as first sensing information.

In a first state (Case 1) 501 (e.g., a general state), the processor 120 may analyze a pulse wave 510 that is included in the first sensing information (e.g., the PPG) obtained by the first sensor 190. The processor 120 may divide the pulse wave 510 into two sub-waves (e.g., a first sub-wave 511 and a second sub-wave 512) of a Gaussian model.

The first sub-wave 511 may be a forward wave that is generated directly by a pulsation occurring in the heart. The second sib-wave 512 may be a reflected wave that is generated as the forward wave is reflected to vessel walls and other organs and is transmitted.

The processor 120 may calculate feature values representative of the waveform from each waveform. For example, the processor 120 may calculate maximum amplitudes P1 and P2. In FIG. 5, the maximum amplitudes P1 and P2 are mainly described, but the disclosure is not limited thereto. The processor 120 may calculate a vascular resistance parameter by using various feature values, such as time duration and waveform area, in addition to the max amplitude.

According to various embodiments of the disclosure, the processor 120 may determine the vascular resistance parameter as a ratio of the maximum amplitude P2 of the first sub-wave 511 and the maximum amplitude P1 of the second sub-wave 512 (the vascular resistance=P2/P1).

According to various embodiments of the disclosure, the processor 120 may normalize the vascular resistance parameter to a vascular resistance value (vascular resistance calibration) at the time of calibration. The processor 120 may calculate a value that changes based on the vascular resistance value of '1' at the time of the calibration.

According to various embodiments of the disclosure, when the blood flow rate of the user is changed from the first state 501 (e.g., general state) to a second state 502 (e.g., a high blood pressure state), the processor 120 may divide a pulse wave 520 into two sub-waves (e.g., a first sub-wave 521 and a second sub-wave 522) of the Gaussian model.

The processor 120 may calculate max amplitudes P1' and P2'. The processor 120 may determine the vascular resistance parameter as a ratio of the maximum amplitude P2' of the second sub-wave 512 and the maximum amplitude P r of the first sub-wave 511 (vascular resistance=P2'/P1').

The maximum amplitude P2' of the second sub-wave 522 of the second state (Case 2) 502 (e.g., a high blood pressure state) may be greater than the maximum amplitude P2 of the second sub-wave 512 of the first state 501. Accordingly, the vascular resistance parameter of the second state 502 (e.g., the high blood pressure state) may be greater than the vascular resistance parameter of the first state 501.

FIG. 6 is a diagram illustrating how to calculate a weight based on vascular resistance parameters, according to an embodiment of the disclosure.

Referring to FIG. 6, the processor 120 may calculate a first blood flow rate in the first manner by using first sensing information (e.g., a PPG). The processor 120 may calculate a second blood flow rate in the second manner by using the first sensing information (e.g., a PPG) and second sensing information (e.g., ECG). The processor 120 may determine a weight of each of the first blood flow rate and the second blood flow rate, based on the vascular resistance parameter.

The processor 120 may in advance store a change in a weight value $W_1$ to be applied to the first blood flow rate and a change in a weight value $W_2$ to be applied to the second blood flow rate due to a change in the vascular resistance parameter. Each of the weight value $W_1$ to be applied to the first blood flow rate and the weight value $W_2$ to be applied to the second blood flow rate is varied from 0 to 1, based on the vascular resistance parameter. The sum of the weight value $W_1$ to be applied to the first blood flow rate and the weight value $W_2$ to be applied to the second blood flow rate may be uniformly maintained.

The case where the weight values $W_1$ and $W_2$ are linearly changed depending on the change of the vascular resistance parameter is described in FIG. 6, but the disclosure is not limited thereto. For example, the weight values $W_1$ and $W_2$ may change nonlinearly depending on the change in the vascular resistance parameter.

According to various embodiments of the disclosure, when the vascular resistance parameter is determined by obtaining the first sensing information (e.g., a PPG), the processor 120 may determine the weight value $W_1$ to be applied to the first blood flow rate and the weight value $W_2$ to be applied to the second blood flow rate. The processor 120 may calculate a corrected blood flow rate, based on the determined first weight $W_1$ and the determined second weight $W_2$.

For example, according to the vascular resistance parameter calculated in the first state 501 (Case 1) of FIG. 5, the weight value $W_1$ may be determined as 0.25, and the weight value $W_2$ may be determined as 0.75. When the first blood flow rate measured in the first manner is 7 m/sec and the second blood flow rate measured in the second manner is 8 m/sec, the corrected blood flow rate may be determined as 7.75 m/sec (=0.25·7 m/sec+0.75·8 m/sec).

For another example, according to the vascular resistance parameter calculated in the second state 502 (Case 2) of FIG. 5, the weight value $W_1$ may be determined as 0.75 and the weight value $W_2$ may be determined as 0.25. When the first blood flow rate measured in the first manner is 7 m/sec and the second blood flow rate measured in the second manner is 8 m/sec, the corrected blood flow rate may be determined as 7.25 m/sec (=0.75·7 m/sec+0.25·8 m/sec).

Figure 7:
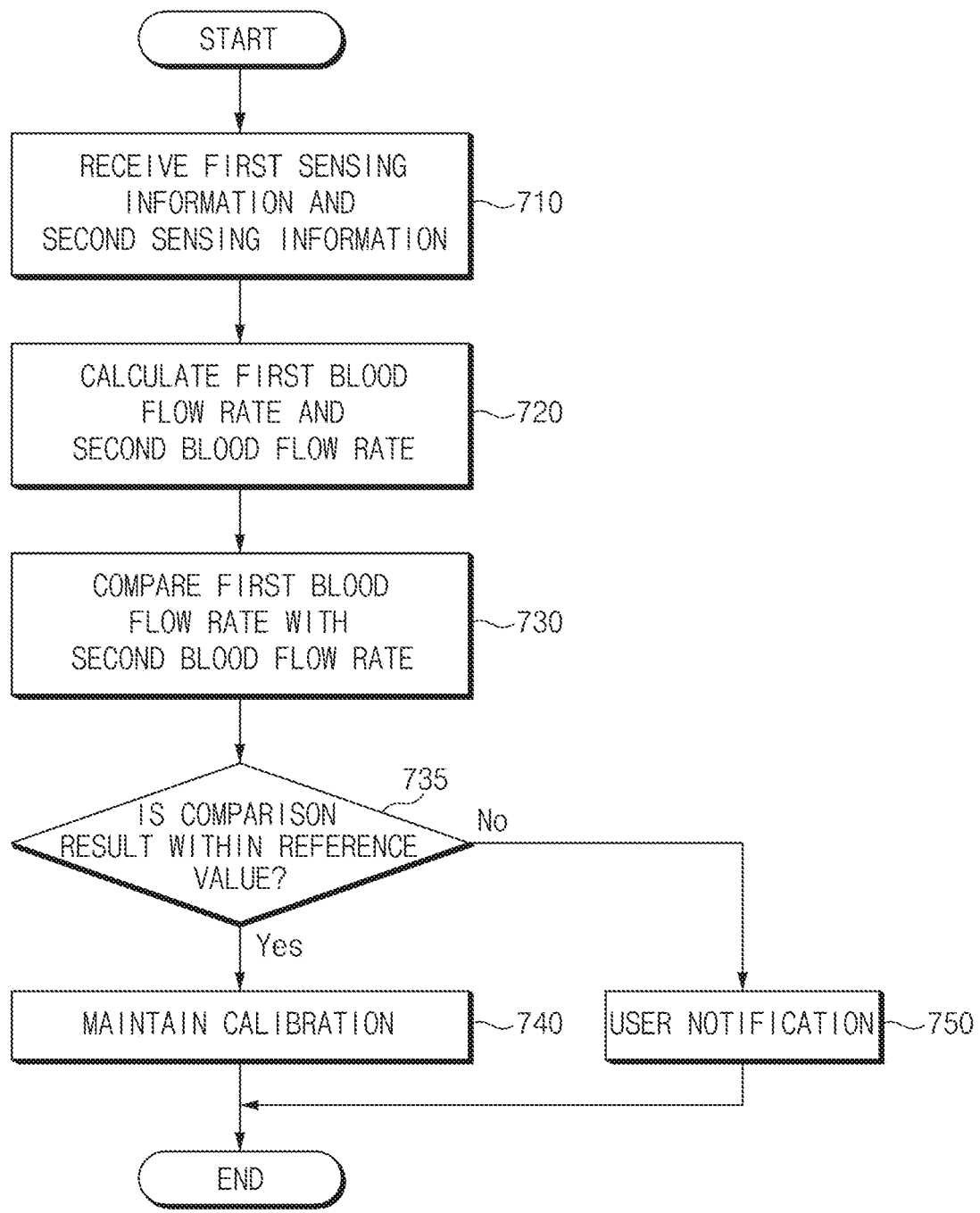
FIG. 7 is a flowchart illustrating a change in a calibration value due to a difference between a first blood flow rate and a second blood flow rate according to an embodiment of the disclosure.

FIG. 7 is a flowchart illustrating a change in a calibration value due to a difference between a first blood flow rate and a second blood flow rate according to an embodiment of the disclosure.

Referring to FIG. 7, in operation 710, the processor 120 may receive first sensing information and second sensing information from the first sensor 190 and the second sensor 195, respectively.

In operation 720, when each of the first sensing information (e.g., a PPG) and the second sensing information (e.g., ECG) has a quality value capable of calculating a blood flow rate, the processor 120 may respectively calculate a first blood flow rate and a second blood flow rate by using the first manner and the second manner.

In operation 730, the processor 120 may compare the first blood flow rate with the second blood flow rate.

In operation 735, the processor 120 may determine whether a difference value between the first blood flow rate and the second blood flow rate is within a specified reference value.

In operation 740, when the difference value is within the specified reference value, the processor 120 may maintain a current calibration value without modification. The processor 120 may update a reliability index of the calibration.

In operation 750, when the difference is greater than the specified reference value, the processor 120 may generate a notification to the user because there may be an error in the variable setting due to a change in the user's health state or a change in the measurement environment of the electronic device. Alternatively, the processor 120 may guide to recalibrate.

Figure 8:
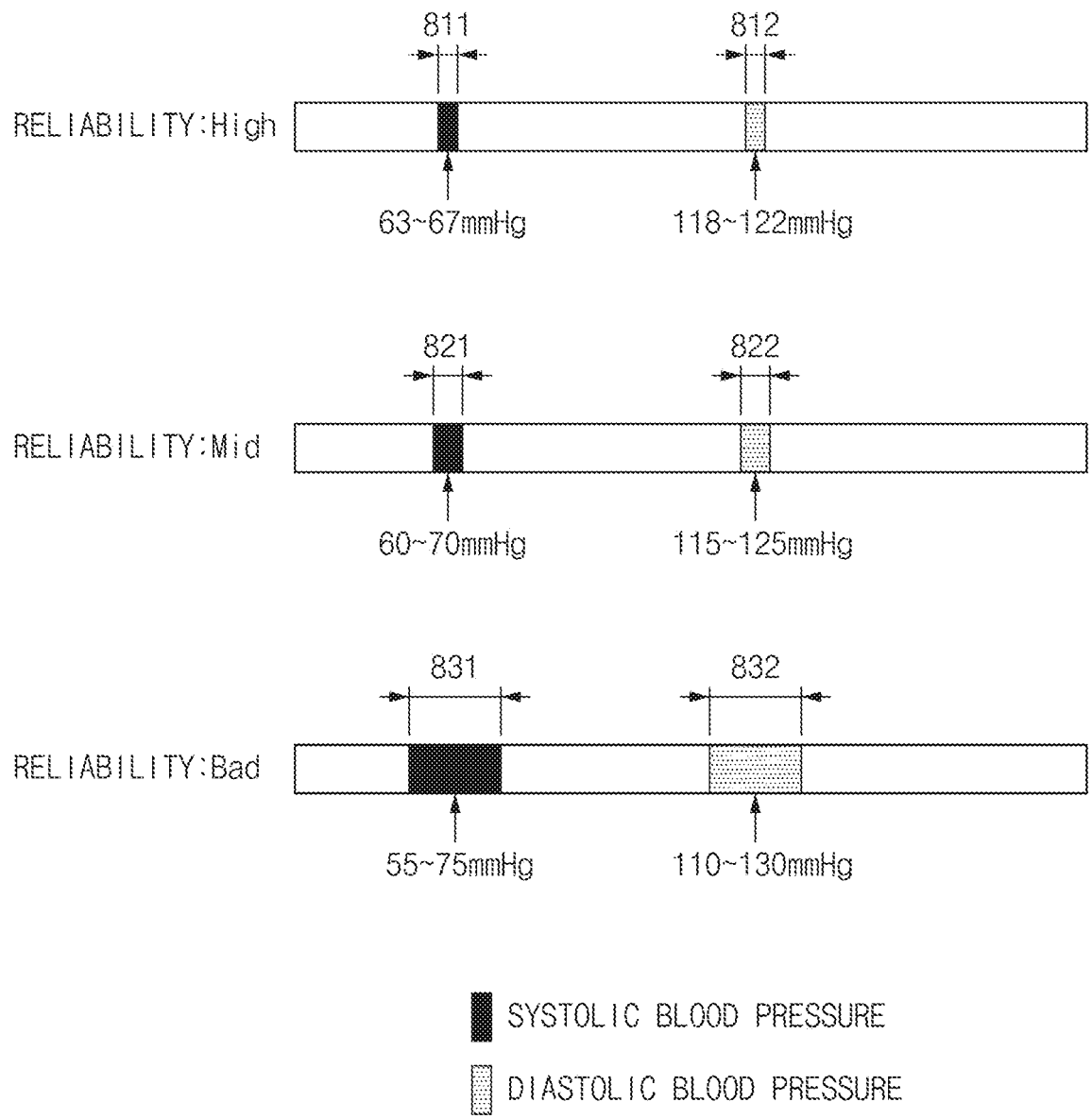
FIG. 8 illustrates a calibration reliability index according to an embodiment of the disclosure.

FIG. 8 illustrates a calibration reliability index according to an embodiment of the disclosure.

Referring to FIG. 8, the processor 120 may divide the reliability index of the calibration into several levels.

The processor 120 may update the step of the reliability index, based on a difference between a first blood flow rate measured in the first manner and a second blood flow rate measured in the second manner.

For example, when the difference between the first blood flow rate measured in the first manner and the second blood flow rate measured in the second manner is within a first reference value (e.g., a first reference value 811 for the systolic heart or a first reference value 812 for diastolic heart), the reliability index may be displayed in a high state. The user may rely on the blood pressure measurement result without a separate re-calibration process.

For another example, when the difference between the first blood flow rate measured in the first manner and the second blood flow rate measured in the second manner exceeds the first reference value 811 or 812 and is within a second reference value (e.g., a second reference value 821 for the systolic heart or a second reference value 822 for the diastolic heart) greater than the first reference value 811 or 812, the reliability index may be displayed in a middle state. The user may decide whether to perform a separate process (re-calibration).

For another example, when the difference between the first blood flow rate measured in the first manner and the second blood flow rate measured in the second manner exceeds the second reference value 821 or 822 and is within a third reference value (e.g., a third reference value 831 for the systolic heart or a third reference value 832 for the diastolic heart), the reliability index may be displayed in a low state. The processor 120 may guide the user to perform a separate calibration (re-calibration).

Figure 9:
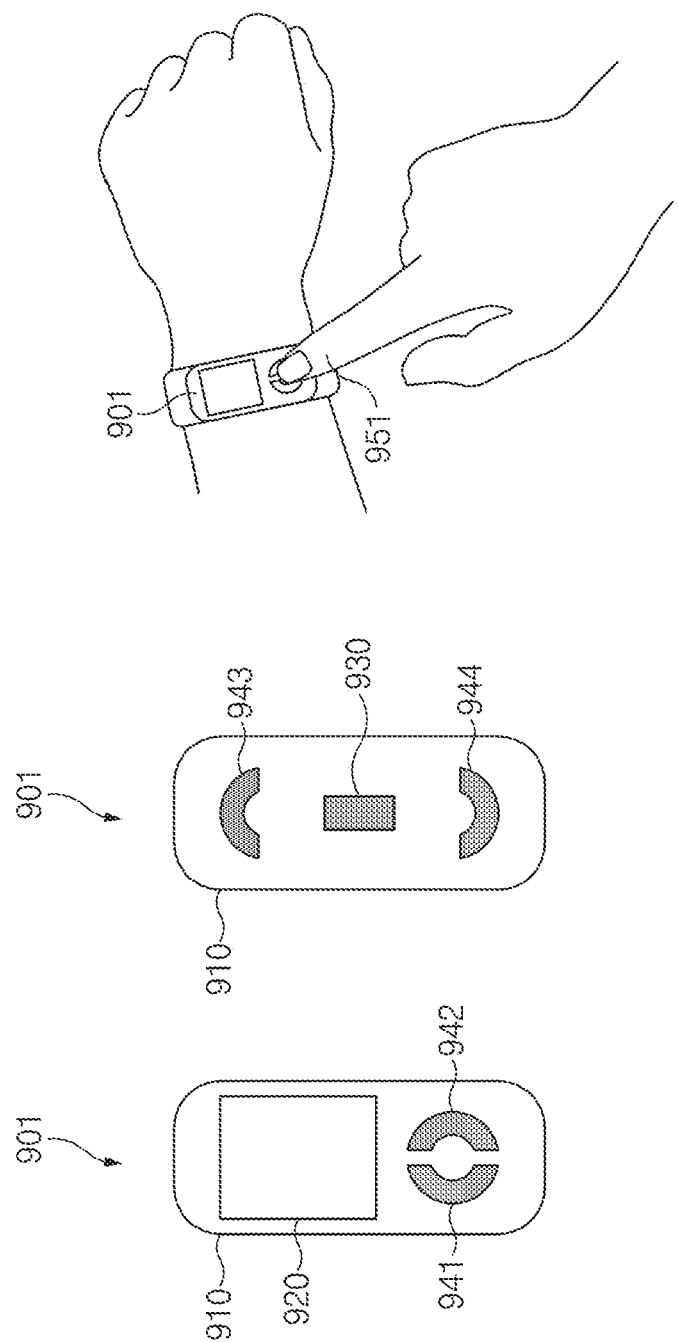
FIG. 9 is a diagram illustrating electrode shapes of a wearable device according to an embodiment of the disclosure.

FIG. 9 is a diagram illustrating electrode shapes of a wearable device according to an embodiment of the disclosure.

Referring to FIG. 9, an electronic device 901 may be a wearable device. The electronic device 901 may include a housing 910, a display 920, a sensor 930, and a plurality of electrodes 940.

The housing 910 may form an appearance of the electronic device 901. Various elements or parts necessary for driving the electronic device 901 may be mounted in the housing 910. The housing 910 may include various components therein, such as a processor, a memory, a printed circuit board, or a battery.

At least a portion of the display 920 may be viewable through a first portion (e.g., a front surface) of the housing 910. The display 920 may display various content, such as text or an image. The display 920 may include a touch panel and may receive a touch input of the user.

The sensor (e.g., PPG sensor) 930 may be exposed through a second portion (e.g., a rear surface) of the housing 910. The sensor (e.g., PPG sensor) 930 may output light of a specified frequency by using a light source and may obtain light reflected from the user's body.

The plurality of electrodes 940 may be in contact with the user's body to obtain an electrical signal. The plurality of electrodes 940 may include a first electrode 941 to a fourth electrode 944. When the plurality of electrodes 940 are in contact with a part of the user's body, the electrocardiogram (e.g., ECG) may be measured based on an electrical signal flowing through the electrodes.

According to various embodiments of the disclosure, the first electrode 941 and the second electrode 942 may be disposed on a first surface on which the display 920 is exposed. The first electrode 941 and the second electrode 942 may be disposed adjacent to each other with the electrodes 941 and 942 spaced from each other as much as a specified interval. For example, the first electrode 941 and the second electrode 942 may be arranged to maintain a distance at which the user may touch his/her one finger 951 on the first electrode 941 and the second electrode 942 at the same time.

According to various embodiments of the disclosure, the case in which the first electrode 941 and the second electrode 942 are disposed on the first surface on which the display 920 is exposed is illustrated in FIG. 9, but the disclosure is not limited thereto. For example, the first electrode 941 and the second electrode 942 may be disposed on a side surface of the housing 910 or may be included in a button part (e.g., a crown).

According to various embodiments of the disclosure, the third electrode 943 and the fourth electrode 944 may be disposed on a second surface opposite to the first surface (a surface opposite to the surface on which the display 920 is exposed). The third electrode 943 and the fourth electrode 944 may be spaced from each other by a specified distance with the sensor 930 interposed therebetween. When the user wears the electronic device 901, the third electrode 943 and the fourth electrode 944 may maintain normal contact with the user's body.

Figure 10:
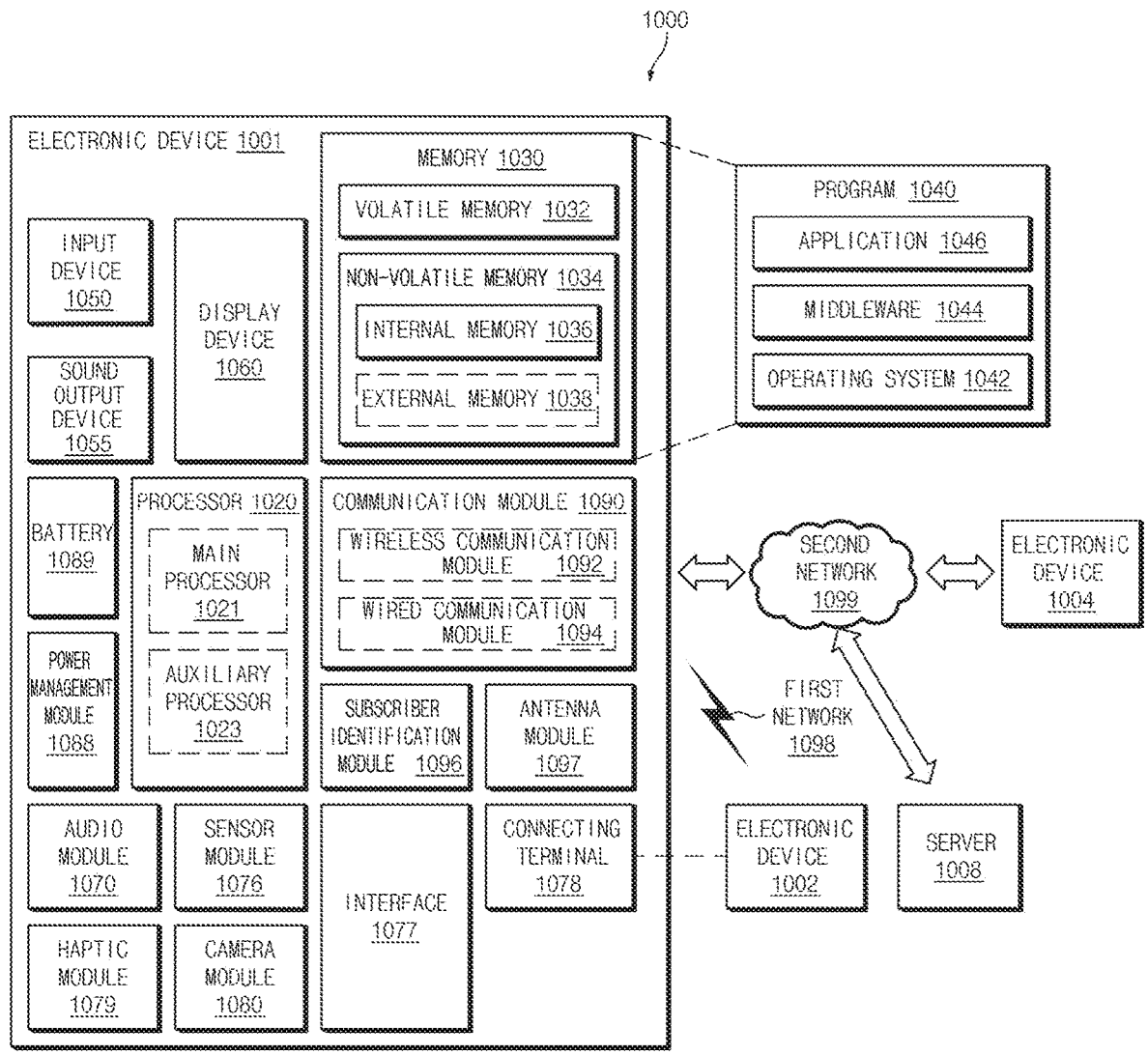
FIG. 10 is illustrating a block diagram of an electronic device in a network environment according to an embodiment of the disclosure.

FIG. 10 is a block diagram illustrating an electronic device in a network environment according to an embodiment of the disclosure.

Referring to FIG. 10, an electronic device 1001 (e.g., the electronic device 101 of FIG. 1) in the network environment 1000 may communicate with an electronic device 1002 via a first network 1098 (e.g., a short-range wireless communication network), or an electronic device 1004 or a server 1008 via a second network 1099 (e.g., a long-range wireless communication network). According to an embodiment of the disclosure, the electronic device 1001 (e.g., the electronic device 101 of FIG. 1) may communicate with the electronic device 1004 via the server 1008. According to an embodiment of the disclosure, the electronic device 1001 may include a processor 1020 (e.g., the processor 120 of FIG. 1), memory 1030 (e.g., the memory 130 of FIG. 1), an input device 1050, a sound output device 1055, a display device 1060 (e.g., the display 160 of FIG. 1), an audio module 1070, a sensor 1076 (e.g., the first sensor 190 or the second sensor 195 of FIG. 1), an interface 1077, a haptic module 1079, a camera module 1080 (e.g., the camera 170 of FIG. 1), a power management module 1088, a battery 1089, a communication module 1090, a subscriber identification module (SIM) 1096, or an antenna module 1097. In some embodiments of the disclosure, at least one (e.g., the display device 1060 (e.g., the display 160 of FIG. 1) or the camera module 1080 (e.g., the camera 170 of FIG. 1)) of the components may be omitted from the electronic device 1001 (e.g., the electronic device 101 of FIG. 1), or one or more other components may be added in the electronic device 1001 (e.g., the electronic device 101 of FIG. 1). In some embodiments of the disclosure, some of the components may be implemented as single integrated circuitry. For example, the sensor 1076 (e.g., the first sensor 190 or the second sensor 195 of FIG. 1) (e.g., a fingerprint sensor, an iris sensor, or an illuminance sensor) may be implemented as embedded in the display device 1060 (e.g., the display 160 of FIG. 1) (e.g., a display).

The processor 1020 (e.g., the processor 120 of FIG. 1) may execute, for example, software (e.g., a program 1040) to control at least one other component (e.g., a hardware or software component) of the electronic device 1001 (e.g., the electronic device 101 of FIG. 1) coupled with the processor 1020 (e.g., the processor 120 of FIG. 1), and may perform various data processing or computation. According to one embodiment of the disclosure, as at least part of the data processing or computation, the processor 1020 (e.g., the processor 120 of FIG. 1) may load a command or data received from another component (e.g., the sensor 1076 (e.g., the first sensor 190 or the second sensor 195 of FIG. 1) or the communication module 1090) in a volatile memory 1032, process the command or the data stored in the volatile memory 1032, and store resulting data in a non-volatile memory 1034. According to an embodiment of the disclosure, the processor 1020 (e.g., the processor 120 of FIG. 1) may include a main processor 1021 (e.g., a central processing unit (CPU) or an application processor (AP)), and an auxiliary processor 1023 (e.g., a graphics processing unit (GPU), an image signal processor (ISP), a sensor hub processor, or a communication processor (CP)) that is operable independently from, or in conjunction with, the main processor 1021. Additionally or alternatively, the auxiliary processor 1023 may be adapted to consume less power than the main processor 1021, or to be specific to a specified function. The auxiliary processor 1023 may be implemented as separate from, or as part of the main processor 1021.

The auxiliary processor 1023 may control at least some of functions or states related to at least one component (e.g., the display device 1060 (e.g., the display 160 of FIG. 1), the sensor 1076 (e.g., the first sensor 190 or the second sensor 195 of FIG. 1), or the communication module 1090) among the components of the electronic device 1001 (e.g., the electronic device 101 of FIG. 1), instead of the main processor 1021 while the main processor 1021 is in an inactive (e.g., sleep) state, or together with the main processor 1021 while the main processor 1021 is in an active state (e.g., executing an application). According to an embodiment of the disclosure, the auxiliary processor 1023 (e.g., an image signal processor or a communication processor) may be implemented as part of another component (e.g., the camera module 1080 (e.g., the camera 170 of FIG. 1) or the communication module 1090) functionally related to the auxiliary processor 1023.

The memory 1030 (e.g., the memory 130 of FIG. 1) may store various data used by at least one component (e.g., the processor 1020 (e.g., the processor 120 of FIG. 1) or the sensor 1076 (e.g., the first sensor 190 or the second sensor 195 of FIG. 1)) of the electronic device 1001 (e.g., the electronic device 101 of FIG. 1). The various data may include, for example, software (e.g., the program 1040) and input data or output data for a command related thererto. The memory 1030 (e.g., the memory 130 of FIG. 1) may include the volatile memory 1032 or the non-volatile memory 1034.

The program 1040 may be stored in the memory 1030 (e.g., the memory 130 of FIG. 1) as software, and may include, for example, an operating system (OS) 1042, middleware 1044, or an application 1046.

The input device 1050 may receive a command or data to be used by other component (e.g., the processor 1020 (e.g., the processor 120 of FIG. 1)) of the electronic device 1001 (e.g., the electronic device 101 of FIG. 1), from the outside (e.g., a user) of the electronic device 1001 (e.g., the electronic device 101 of FIG. 1). The input device 1050 may include, for example, a microphone, a mouse, a keyboard, or a digital pen (e.g., a stylus pen).

The sound output device 1055 may output sound signals to the outside of the electronic device 1001 (e.g., the electronic device 101 of FIG. 1). The sound output device 1055 may include, for example, a speaker or a receiver. The speaker may be used for general purposes, such as playing multimedia or playing record, and the receiver may be used for an incoming call. According to an embodiment of the disclosure, the receiver may be implemented as separate from, or as part of the speaker.

The display device 1060 (e.g., the display 160 of FIG. 1) may visually provide information to the outside (e.g., a user) of the electronic device 1001 (e.g., the electronic device 101 of FIG. 1). The display device 1060 (e.g., the display 160 of FIG. 1) may include, for example, a display, a hologram device, or a projector and control circuitry to control a corresponding one of the display, hologram device, and projector. According to an embodiment of the disclosure, the display device 1060 (e.g., the display 160 of FIG. 1) may include touch circuitry adapted to detect a touch, or sensor circuitry (e.g., a pressure sensor) adapted to measure the intensity of force incurred by the touch.

The audio module 1070 may convert a sound into an electrical signal and vice versa. According to an embodiment of the disclosure, the audio module 1070 may obtain the sound via the input device 1050, or output the sound via the sound output device 1055 or an external electronic device (e.g., an electronic device 1002) (e.g., speaker of headphone) directly (e.g., wiredly) or wirelessly coupled with the electronic device 1001 (e.g., the electronic device 101 of FIG. 1).

The sensor 1076 (e.g., the first sensor 190 or the second sensor 195 of FIG. 1) may detect an operational state (e.g., power or temperature) of the electronic device 1001 (e.g., the electronic device 101 of FIG. 1) or an environmental state (e.g., a state of a user) external to the electronic device 1001, and then generate an electrical signal or data value corresponding to the detected state. According to an embodiment of the disclosure, the sensor 1076 (e.g., the first sensor 190 or the second sensor 195 of FIG. 1) may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 1077 may support one or more specified protocols to be used for the electronic device 1001 (e.g., the electronic device 101 of FIG. 1) to be coupled with the external electronic device (e.g., the electronic device 1002) directly (e.g., wiredly) or wirelessly. According to an embodiment of the disclosure, the interface 1077 may include, for example, a high definition multimedia interface (HDMI), a universal serial bus (USB) interface, a secure digital (SD) card interface, or an audio interface.

A connecting terminal 1078 may include a connector via which the electronic device 1001 (e.g., the electronic device 101 of FIG. 1) may be physically connected with the external electronic device (e.g., the electronic device 1002). According to an embodiment of the disclosure, the connecting terminal 1078 may include, for example, a HDMI connector, a USB connector, a SD card connector, or an audio connector (e.g., a headphone connector).

The haptic module 1079 may convert an electrical signal into a mechanical stimulus (e.g., a vibration or a movement) or electrical stimulus which may be recognized by a user via his tactile sensation or kinesthetic sensation. According to an embodiment of the disclosure, the haptic module 1079 may include, for example, a motor, a piezoelectric element, or an electric stimulator.

The camera module 1080 (e.g., the camera 170 of FIG. 1) may capture a still image or moving images. According to an embodiment of the disclosure, the camera module 1080 (e.g., the camera 170 of FIG. 1) may include one or more lenses, image sensors, image signal processors, or flashes.

The power management module 1088 may manage power supplied to the electronic device 1001 (e.g., the electronic device 101 of FIG. 1). According to one embodiment of the disclosure, the power management module 1088 may be implemented as at least part of, for example, a power management integrated circuit (PMIC).

The battery 1089 may supply power to at least one component of the electronic device 1001 (e.g., the electronic device 101 of FIG. 1). According to an embodiment of the disclosure, the battery 1089 may include, for example, a primary cell which is not rechargeable, a secondary cell which is rechargeable, or a fuel cell.

The communication module 1090 may support establishing a direct (e.g., wired) communication channel or a wireless communication channel between the electronic device 1001 (e.g., the electronic device 101 of FIG. 1) and the external electronic device (e.g., the electronic device 1002, the electronic device 1004, or the server 1008) and performing communication via the established communication channel. The communication module 1090 may include one or more communication processors that are operable independently from the processor 1020 (e.g., the processor 120 of FIG. 1) (e.g., the application processor (AP)) and supports a direct (e.g., wired) communication or a wireless communication. According to an embodiment of the disclosure, the communication module 1090 may include a wireless communication module 1092 (e.g., a cellular communication module, a short-range wireless communication module, or a global navigation satellite system (GNSS) communication module) or a wired communication module 1094 (e.g., a local area network (LAN) communication module or a power line communication (PLC) module). A corresponding one of these communication modules may communicate with the external electronic device 1004 via the first network 1098 (e.g., a short-range communication network, such as Bluetooth™, wireless-fidelity (Wi-Fi) direct, or infrared data association (IrDA)) or the second network 1099 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 1092 may identify and authenticate the electronic device 1001 (e.g., the electronic device 101 of FIG. 1) in a communication network, such as the first network 1098 or the second network 1099, using subscriber information (e.g., international mobile subscriber identity (IMSI)) stored in the subscriber identification module 1096.

The antenna module 1097 may transmit or receive a signal or power to or from the outside (e.g., the external electronic device) of the electronic device 1001. According to an embodiment of the disclosure, the antenna module 1097 may include an antenna including a radiating element composed of a conductive material or a conductive pattern formed in or on a substrate (e.g., PCB). According to an embodiment of the disclosure, the antenna module 1097 may include a plurality of antennas. In such a case, at least one antenna appropriate for a communication scheme used in the communication network, such as the first network 1098 or the second network 1099, may be selected, for example, by the communication module 1090 from the plurality of antennas. The signal or the power may then be transmitted or received between the communication module 1090 and the external electronic device via the selected at least one antenna. According to an embodiment of the disclosure, another component (e.g., a radio frequency integrated circuit (RFIC)) other than the radiating element may be additionally formed as part of the antenna module 1097.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment of the disclosure, commands or data may be transmitted or received between the electronic device 1001 (e.g., the electronic device 101 of FIG. 1) and the external electronic device 1004 via the server 1008 coupled with the second network 1099. Each of the external electronic devices 1002 and 1004 may be a device of a same type as, or a different type, from the electronic device 1001 (e.g., the electronic device 101 of FIG. 1). According to an embodiment of the disclosure, all or some of operations to be executed at the electronic device 1001 (e.g., the electronic device 101 of FIG. 1) may be executed at one or more of the external electronic devices 1002, 1004, or 1008. For example, when the electronic device 1001 (e.g., the electronic device 101 of FIG. 1) should perform a function or a service automatically, or in response to a request from a user or another device, the electronic device 1001 (e.g., the electronic device 101 of FIG. 1), instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 1001 (e.g., the electronic device 101 of FIG. 1). The electronic device 1001 (e.g., the electronic device 101 of FIG. 1) may provide the outcome, with or without further processing of the outcome, as at least part of a reply to the request. To that end, a cloud computing, distributed computing, or client-server computing technology may be used, for example.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment of the disclosure, the module may be implemented in a form of an application-specific integrated circuit (ASIC).

Various embodiments as set forth herein may be implemented as software (e.g., the program 1040) including one or more instructions that are stored in a storage medium (e.g., internal memory 1036 or external memory 1038) that is readable by a machine (e.g., the electronic device 1001 (e.g., the electronic device 101 of FIG. 1)). For example, a processor (e.g., the processor 1020 (e.g., the processor 120 of FIG. 1)) of the machine (e.g., the electronic device 1001 (e.g., the electronic device 101 of FIG. 1)) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a compiler or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment of the disclosure, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

An electronic device (e.g., the electronic device 101 of FIG. 1) according to various embodiments includes a housing, a display (e.g., the display 160 of FIG. 1) that is visible through a first portion of the housing, a first sensor that uses a light source that is exposed through a second portion of the housing, at least one conductive electrode (e.g., the second sensor 195 of FIG. 1) that is disposed outside the housing or on the display (e.g., the display 160 of FIG. 1), a processor (e.g., the processor 120 of FIG. 1) that is disposed inside the housing and operatively connected to the first sensor (e.g., the first sensor 190 of FIG. 1), the conductive electrode (e.g., the second sensor 195 of FIG. 1), and the display (e.g., the display 160 of FIG. 1), and a memory (e.g., the memory 130 of FIG. 1) that is disposed inside the housing and operatively connected to the processor (e.g., the processor 120 of FIG. 1), and wherein the memory (e.g., the memory 130 of FIG. 1) may store instructions that, when executed, cause the processor (e.g., the processor 120 of FIG. 1) to receive first data from the first sensor (e.g., the first sensor 190 of FIG. 1), to receive second data from the conductive electrode (e.g., the second sensor 195 of FIG. 1), to process the first data by using a first pulse wave velocity (PWV) manner, based at least in part on a correlation of waveforms included in the first data, to process the first data and the second data by using a second PWV manner different from the first PWV manner, based at least in part on frequencies associated with the first data and the second data, to calculate a first weight associated with the first PWV manner and a second weight associated with the second PWV manner, based at least in part on a ratio of the waveforms included in the first data, to calculate a blood pressure value, based on the first weight and the second weight, and to display the calculated blood pressure on the display (e.g., the display 160 of FIG. 1).

According to various embodiments of the disclosure, the instructions, when executed, may cause the processor (e.g., the processor 120 of FIG. 1) to compare the correlation of the waveforms with a first threshold, and compare magnitudes of the frequencies with a second threshold.

According to various embodiments of the disclosure, the instructions may cause the processor (e.g., the processor 120 of FIG. 1) to provide a notification through a user interface, when the correlation of the waveforms is below the first threshold and the magnitudes of the frequencies are below the second threshold.

According to various embodiments of the disclosure, the first PWV manner include an aortic (Ao) PWV manner, and the second PWV manner may include a pulse arrival time (PAT) PWV manner.

According to various embodiments of the disclosure, the electronic device further includes an acceleration sensor and a gyro sensor located inside the electronic device, and the instructions may cause the processor (e.g., the processor 120 of FIG. 1) to estimate the blood pressure value, based at least in part on a value of the acceleration sensor and/or a value of the gyro sensor.

An electronic device (e.g., the electronic device 101 of FIG. 1) according to various embodiments includes a memory (e.g., the memory 130 of FIG. 1), a first sensor (e.g., the first sensor 190 of FIG. 1) that obtains a first sensing information, using a light source, a second sensor (e.g., the second sensor 195 of FIG. 1) that receives a second sensing information by using a plurality of electrodes, and a processor (e.g., the processor 120 of FIG. 1), and wherein the memory (e.g., the memory 130 of FIG. 1) may store instructions that, when executed, cause the processor (e.g., the processor 120 of FIG. 1) to obtain the first sensing information and the second sensing information within a specified time, to determine whether the first sensing information and the second sensing information are valid, to calculate a first blood flow rate in a first manner, based on the first sensing information, and calculate a second blood flow rate in a second manner, based on the first sensing information and the second sensing information, when the first sensing information and the second sensing information are valid, to determine a first weight for the first blood flow rate and a second weight for the second blood flow rate by using a parameter related to a vascular resistance, and to determine a corrected blood flow rate, based on the first weight and the second weight.

According to various embodiments of the disclosure, the instructions may cause the processor (e.g., the processor 120 of FIG. 1) to divide a pulse waveform included in the first sensing information into a first sub-waveform and a second sub-waveform, and to determine the parameter, based on characteristic values of the first sub-waveform and the second sub-waveform.

According to various embodiments of the disclosure, the instructions may cause the processor (e.g., the processor 120 of FIG. 1) to determine the parameter, based on a ratio of a maximum magnitude of the second sub-waveform to a maximum magnitude of the first sub-waveform.

According to various embodiments of the disclosure, the instructions may cause the processor (e.g., the processor 120 of FIG. 1) to automatically obtain the first sensing information by using the first sensor (e.g., the first sensor 190 of FIG. 1), based on a specified period.

According to various embodiments of the disclosure, the instructions may cause the processor (e.g., the processor 120 of FIG. 1) to obtain the second sensing information by using the second sensor (e.g., the second sensor 195 of FIG. 1), when a user input occurs at each of the plurality of electrodes for a specified time or more.

According to various embodiments of the disclosure, the instructions may cause the processor (e.g., the processor 120 of FIG. 1) to determine whether the first sensing information and the second sensing information are valid, by comparing the first sensing information and the second sensing information with a pre-stored pattern or a pre-stored reference value.

According to various embodiments of the disclosure, the instructions may cause the processor (e.g., the processor 120 of FIG. 1) to determine a reliability index of calibration, based on a difference between the first blood flow rate and the second blood flow rate.

According to various embodiments of the disclosure, the first sensor (e.g., the first sensor 190 of FIG. 1) may include a plurality of light sources that have a plurality of wavelength bands, a light receiver that obtains reflected light in which light generated by the plurality of light sources is reflected by an external object, and a control circuit that controls the plurality of light sources and the light receiver.

According to various embodiments of the disclosure, the first sensor (e.g., the first sensor 190 of FIG. 1) may include a photoplethysmography (PPG) sensor, and the second sensor (e.g., the second sensor 195 of FIG. 1) may include an electrocardiography (ECG) sensor.

According to various embodiments of the disclosure, the first manner may include an aortic pulse wave velocity (AoPWV) manner, and the second manner may include a pulse arrival time (PAT) pulse wave velocity manner.

A blood pressure measuring method performed in an electronic device (e.g., the electronic device 101 of FIG. 1) according to various embodiments may include receiving first data from a first sensor that uses a light source of the electronic device (e.g., the electronic device 101 of FIG. 1), receiving second data from at least one or more conductive electrodes (e.g., the second sensor 195 of FIG. 1) that are exposed to the outside of electronic device (e.g., the electronic device 101 of FIG. 1), processing the first data by using a first pulse wave velocity (PWV) manner, based at least in part on a correlation of waveforms included in the first data, processing the first data and the second data by using a second PWV manner different from the first PWV manner, based at least in part on frequencies associated with the first data and the second data, calculating a first weight associated with the first PWV manner and a second weight associated with the second PWV manner, based at least in part on a ratio of the waveforms included in the first data, calculating a blood pressure value, based at least in part on the first weight and the second weight value, and displaying the calculated blood pressure on a display (e.g., the display 160 of FIG. 1).

According to various embodiments of the disclosure, the processing of the first data may include comparing the correlation of the waveforms with a first threshold value.

According to various embodiments of the disclosure, the processing of the first data and the second data may include comparing magnitudes of the frequencies with a second threshold value.

According to various embodiments of the disclosure, the method may further include providing a notification through a user interface, when the correlation of the waveforms is below a first threshold and the magnitudes of the frequencies are below a second threshold.

According to various embodiments of the disclosure, the calculating of the blood pressure value may include estimating the blood pressure value, based at least in part on a value of an acceleration sensor and/or a value of a gyro sensor of the electronic device (e.g., the electronic device 101 of FIG. 1).

According to various embodiments of the disclosure, each component (e.g., a module or a program) of the above-described components may include a single entity or multiple entities. According to various embodiments of the disclosure, one or more of the above-described components may be omitted, or one or more other components may be added. Alternatively or additionally, a plurality of components (e.g., modules or programs) may be integrated into a single component. In such a case, according to various embodiments of the disclosure, the integrated component may still perform one or more functions of each of the plurality of components in the same or similar manner as they are performed by a corresponding one of the plurality of components before the integration. According to various embodiments of the disclosure, operations performed by the module, the program, or another component may be carried out sequentially, in parallel, repeatedly, or heuristically, or one or more of the operations may be executed in a different order or omitted, or one or more other operations may be added.

An electronic device according to the embodiments disclosed in the disclosure may apply various manners (e.g., AoPWA or PAT) of the PWV to blood pressure measurement in various forms according to a situation.

An electronic device according to the embodiments disclosed in the disclosure may increase the accuracy of blood pressure measurement through weight calculation and reliability calculation on the blood flow rate calculated in each manner.

An electronic device according to the embodiments disclosed in the disclosure may improve accuracy and convenience of a PWV-based blood pressure estimation in a high level, and may notify a user of a reliability and an update cycle of calibration.

In addition, various effects may be provided that are identified directly or indirectly through this document.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. An electronic device comprising:
a display;
a memory;
a first sensor configured to obtain a first sensing information, using a light source;
a second sensor configured to receive a second sensing information by using a plurality of electrodes; and
at least one processor,
wherein the memory stores instructions that, when executed, cause the at least one processor to:
obtain the first sensing information and the second sensing information within a specified time,
calculate a first blood flow rate in a first manner, based on the first sensing information, and calculate a second blood flow rate in a second manner, based on the first sensing information and the second sensing information,
calculate a vascular resistance parameter based on the first sensing information,
determine a first weight for the first blood flow rate and a second weight for the second blood flow rate based on the vascular resistance parameter,
calculate a corrected blood flow rate based on the first blood flow rate, the first weight, the second blood flow rate, and the second weight,
calculate a blood pressure value using the corrected blood flow rate,
when a difference between the first blood flow rate and the second blood flow rate is less than a specified reference value, maintain a calibration value, update a reliability index of the calibration value based on a change of the calibration value, and display the calculated blood pressure value on the display, and the reliability index of the calibration value based on the difference between the first blood flow rate and the second blood flow rate, and
change the calibration value when the difference between the first blood flow rate and the second blood flow rate is greater than the specified reference value.

2. The electronic device of claim 1, wherein the instructions cause the at least one processor to:
divide a pulse waveform included in the first sensing information into a first sub-waveform and a second sub-waveform, and
determine the vascular resistance parameter, based on characteristic values of the first sub-waveform and the second sub-waveform.

3. The electronic device of claim 2, wherein the instructions cause the at least one processor to:
determine the vascular resistance parameter, based on a ratio of a maximum magnitude of the second sub-waveform to a maximum magnitude of the first sub-waveform.

4. The electronic device of claim 1, wherein the instructions cause the at least one processor to:
automatically obtain the first sensing information by using the first sensor, based on a specified period.

5. The electronic device of claim 1, wherein the instructions cause the at least one processor to:
obtain the second sensing information by using the second sensor, when a user input occurs at each of the plurality of electrodes for a specified time or more.

6. The electronic device of claim 1, wherein the instructions cause the at least one processor to:
determine whether the first sensing information and the second sensing information are valid, by comparing the first sensing information and the second sensing information with a pre-stored pattern or a pre-stored reference value, and calculate the first blood flow rate and the second blood flow rate, when the first sensing information and the second sensing information are valid.

7. The electronic device of claim 1, wherein the instructions cause the at least one processor to:

determine the reliability index of calibration, based on the difference between the first blood flow rate and the second blood flow rate.

8. The electronic device of claim 1, wherein the first sensor includes:

a plurality of light sources configured to have a plurality of wavelength bands, a light receiver configured to obtain reflected light in which light generated by the plurality of light sources is reflected by an external object, and a control circuit configured to control the plurality of light sources and the light receiver.

9. The electronic device of claim 1, wherein the first sensor includes a photoplethysmography (PPG) sensor, and the second sensor includes an electrocardiography (ECG) sensor.

10. The electronic device of claim 1, wherein the first manner includes an aortic pulse wave velocity (AoPWV) manner, and the second manner includes a pulse arrival time (PAT) pulse wave velocity manner.

11. A blood pressure measuring method performed in an electronic device, the method comprising:

obtaining first sensing information from a first sensor module that uses a light source and is included in the electronic device within a specified time;

obtaining second sensing information from a second sensor module that using a plurality of electrodes that are exposed to an outside surface of the electronic device;

calculating a first blood flow rate in a first manner, based on the first sensing information, and calculating a second blood flow rate in a second manner, based on the first sensing information and the second sensing information;

calculating a vascular resistance parameter based on the first sensing information;

determining a first weight for the first blood flow rate and a second weight for the second blood flow rate based on the vascular resistance parameter;

calculating a corrected blood flow rate based on the first blood flow rate, the first weight, the second blood flow rate, and the second weight;

calculating a blood pressure value using the corrected blood flow rate;

when a difference between the first blood flow rate and the second blood flow rate is less than a specified reference value, maintaining a calibration value, updating a reliability index of the calibration value based on a change of the calibration value, and displaying the calculated blood pressure value on a display of the electronic device, and the reliability index of the calibration value based on the difference between the first blood flow rate and the second blood flow rate; and changing the calibration value when the difference between the first blood flow rate and the second blood flow rate is greater than the specified reference value.

12. The method of claim 11, wherein the determining the first weight and the second weight includes:

dividing a pulse waveform included in the first sensing information into a first sub-waveform and a second sub-waveform, and determining the vascular resistance parameter, based on characteristic values of the first sub-waveform and the second sub-waveform.

13. The method of claim 12, wherein the determining the vascular resistance parameter includes:

determining the vascular resistance parameter, based on a ratio of a maximum magnitude of the second sub-waveform to a maximum magnitude of the first sub-waveform.

14. The method of claim 11, wherein the obtaining of the first sensing information includes:

automatically obtaining the first sensing information by using the first sensor module, based on a specified period.

15. The method of claim 11, wherein the obtaining of the second sensing information includes obtaining the second sensing information by using the second sensor module, when a user input occurs at each of the plurality of electrodes for a specified time or more.

* * * * *